(12) United States Patent
Barreca et al.

(10) Patent No.: US 11,926,586 B2
(45) Date of Patent: Mar. 12, 2024

(54) PROCESS FOR THE PREPARATION OF FERRIC ORGANIC COMPOUNDS

(71) Applicant: QUÍMICA SINTÉTICA, S.A., Alcalá de Henares (ES)

(72) Inventors: Giuseppe Barreca, Sirtori (IT); Luca Carcone, Milan (IT); Norberto Masciocchi, Como (IT)

(73) Assignee: QUÍMICA SINTÉTICA, S.A., Alcalá de Henares (ES)

( * ) Notice: Subject to any disclaimer, the term of this patent is extended or adjusted under 35 U.S.C. 154(b) by 19 days.

(21) Appl. No.: 17/774,134

(22) PCT Filed: Nov. 6, 2020

(86) PCT No.: PCT/EP2020/081261
§ 371 (c)(1),
(2) Date: May 3, 2022

(87) PCT Pub. No.: WO2021/089766
PCT Pub. Date: May 14, 2021

(65) Prior Publication Data
US 2022/0396542 A1   Dec. 15, 2022

(30) Foreign Application Priority Data

Nov. 8, 2019   (EP) ..................... 19382981

(51) Int. Cl.
*C07C 51/41*   (2006.01)
*C07F 15/02*   (2006.01)

(52) U.S. Cl.
CPC .......... *C07C 51/418* (2013.01); *C07F 15/025* (2013.01)

(58) Field of Classification Search
None
See application file for complete search history.

(56) References Cited

U.S. PATENT DOCUMENTS

2018/0222836 A1* 8/2018 Smart ..................... A61P 7/08
2020/0331943 A1* 10/2020 Miyaoku ............... C07F 15/025

FOREIGN PATENT DOCUMENTS

| WO | WO 2004/074444 A2 | 9/2004 |
| WO | WO 2012/099139 A1 | 7/2012 |
| WO | WO 2015/110968 A1 | 7/2015 |
| WO | WO 2016/098131 A2 | 6/2016 |
| WO | WO 2016/162888 A1 | 10/2016 |
| WO | WO 2017/021921 A1 | 2/2017 |
| WO | WO 2019/093491 A1 | 5/2019 |

OTHER PUBLICATIONS

International Search Report and Written Opinion dated Jan. 21, 2021 for International Application No. PCT/EP2020/081261, 12 pages.

* cited by examiner

*Primary Examiner* — Amy C Bonaparte
(74) *Attorney, Agent, or Firm* — Squire Patton Boggs (US) LLP

(57) ABSTRACT

A highly pure form of ferric citrate and an industrially viable and advantageous process for its preparation are described.

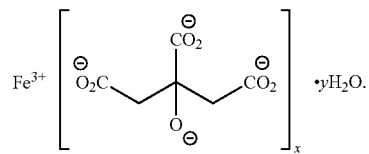

12 Claims, 1 Drawing Sheet

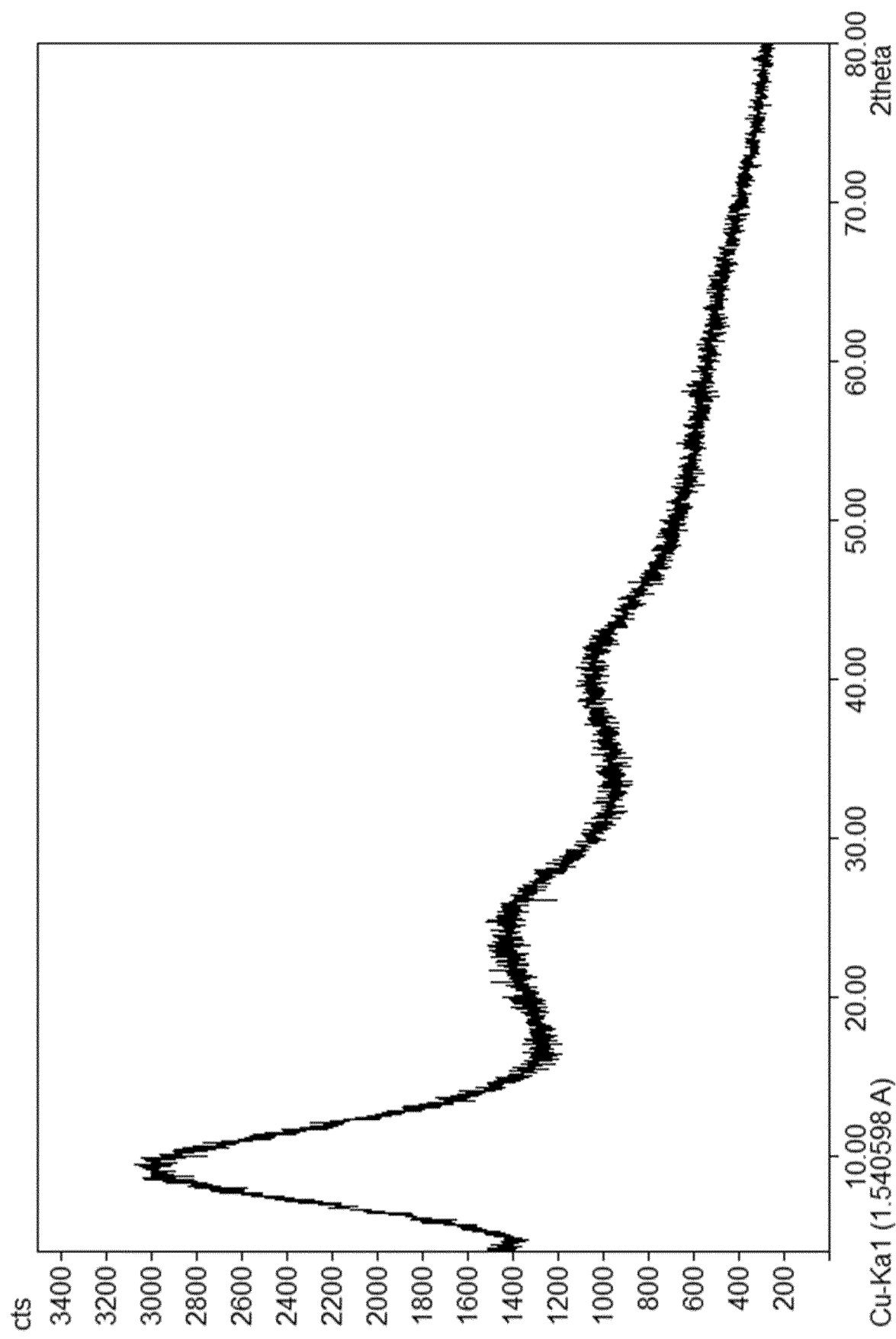

PROCESS FOR THE PREPARATION OF FERRIC ORGANIC COMPOUNDS

CROSS-REFERENCE

This application is a national-stage filing under 37 USC 371(c) of International Application No. PCT/EP2020/081261, filed Nov. 6, 2020, which claims priority to and the benefit of European Patent Application EP19382981.9, filed Nov. 8, 2019, and the contents of each are herein incorporated by reference in their entirety for all purposes.

FIELD OF THE INVENTION

The present invention relates to a highly pure form of ferric citrate, to an industrially viable and advantageous process for its preparation and to the use of such form as a medicament, e.g. in the treatment of hyperphosphatemia and metabolic acidosis.

STATE OF THE ART

Ferric citrate is the INN denomination assigned to the compound having chemical name iron (III)-(2-hydroxy-1,2,3-propanetricarboxylic acid)$_x \cdot (H_2O)_y$ and an undefined molecular ratio. Its chemical structure is:

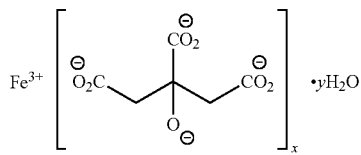

Coordination complexes of ferric citrate and ferric containing compounds are inorganic, iron-based compounds that have the capacity to bind to phosphates and to form non-absorbable complexes with phosphates. Such ferric compounds are useful for the treatment of hyperphosphatemia and metabolic acidosis.

Hyperphosphatemia is associated with severe complications, such as hypocalcemia, decreasing of vitamin-D production, metastatic calcification. Hyperphosphatemia is also contributing to the increased incidence of cardiovascular disease among dialysis-dependent patients and can result in bone pathology.

Pharmaceutical grade ferric citrate having an intrinsic dissolution rate between 1.9 and 4.0 mg/cm$^2$/min and a BET active surface area exceeding 16 m$^2$/g was disclosed in the international patent application WO 2004/074444 A2. The process described therein entails, as key steps, (i) treatment of ferric chloride hexahydrate (FeCl$_3$.6H$_2$O) with a 5M solution of sodium hydroxide in water so as to produce a polyiron oxide colloidal suspension of ferric hydroxide; (ii) filter the suspension through a 1 mm stainless steel filter to breakup aggregates and remove large particles of ferric hydroxide precipitate; (iii) centrifugate the ferric hydroxide suspension; (iv) resuspend ferric hydroxide precipitate in water and recentrifugate it so as to remove the water soluble impurities; (v) add citric acid to the aqueous suspension and maintain under stirring at 80-90° C. until dissolution of the ferric hydroxide precipitate is observed; (vi) monitor that the pH of the mixture is from 0.8 to 1.5; (vii) centrifugate it so as to remove insoluble materials; (viii) add acetone to the surnatant so as to obtain a precipitate; and (ix) collect the pharmaceutical grade ferric citrate.

Further procedures for the preparation of ferric citrate and involving the isolation of ferric hydroxide were disclosed in international patent applications WO 2012/099139 A1, WO 2016/098131 A2, WO 2017/021921 A1 and WO 2019/093491 A1.

On industrial scale, the use of these strategies has several drawbacks ensuing, e.g., from the necessity to isolate ferric hydroxide from a polyiron oxide colloidal suspension containing it.

Given that colloidal suspensions are composed of particles having diameters ranging from 10$^{-7}$ to 10$^{-4}$ cm and that the effect of gravity on these particles is very little, when trying to isolate ferric hydroxide particles it was experimentally observed that they tend not to settle down at the bottom of the container thus making their isolation via filtration very hard, at least insofar as specialized equipments (e.g., industrial centrifuges) are not used.

An alternative procedure partially addressing these drawbacks was described in the international patent application WO 2016/162888 A1 as involving the treatment of a polyiron oxide colloidal suspension, in turn prepared by reacting ferric chloride hexahydrate with a solution of sodium carbonate in water, with a coagulating agent (particularly an aqueous solution of polydiallyldimethylammonium chloride).

In addition to not avoiding the isolation of ferric hydroxide from a water dispersion thereof (the wek cake resulting after the addition of the coagulating agent is triturated in water at 40-60° C.), this reaction necessarily involves the use of at least one coagulating agent, which must be disposed of properly, resulting in additional costs.

Another procedure for the preparation of pharmaceutical grade ferric citrate was disclosed in the international patent application WO 2015/110968 A1 and entailed the direct treatment of an aqueous solution of sodium citrate with ferric chloride hexahydrate.

Although being an interesting approach, this is not practical for multikilogram synthesis—e.g. because of the need to further treat the resulting ferric citrate with an agent able to remove the inorganic impurities (e.g., sodium chloride) entrapped therein.

Object of this invention is, therefore, to provide a new method for the preparation of ferric organic compounds, in particular ferric (III) citrate, avoiding the formation of colloidal suspensions and providing it with yields and purity adequate for pharmaceutical use.

SUMMARY OF THE INVENTION

These objectives, and others which will be made evident hereunder, are achieved by means of the present invention, which, in an aspect, relates to a process for the preparation of a high-purity ferric citrate comprising the following steps:
 a) bringing into contact ferric acetylacetonate and citric acid in at least one liquid medium so as to obtain a mixture;
 b) heating the mixture obtained in step a) to a temperature ranging from 35° C. to the reflux temperature of the at least one medium used so as to obtain a solution of ferric citrate in said medium;
 c) bringing into contact the solution of ferric citrate with an antisolvent so as to cause its precipitation; and
 d) isolating and, optionally, drying it.

In another aspect, the present invention relates to a high purity ferric citrate complex obtainable by the process described above.

In another aspect, the present invention provides said high purity ferric citrate complex for use as a medicament.

In another aspect, the present invention provides the use of said high purity ferric citrate complex for the preparation of a medicament.

In an aspect, the present invention provides a pharmaceutical composition comprising the high purity ferric citrate complex as described above and, optionally, at least one pharmaceutically acceptable carrier.

BRIEF DESCRIPTION OF THE DRAWINGS

FIG. 1 depicts the X-Ray powder diffractogram of the high purity ferric citrate of the invention.

DETAILED DESCRIPTION OF THE INVENTION

All terms used in the present application, unless otherwise indicated, must be interpreted in their ordinary meaning as known in the technical field. Other more specific definitions for some terms used in the present application are given below and are intended to be applied uniformly to the entire description and claims, unless otherwise indicated. The term "ferric citrate" used herein refers to a complex of iron (III), also Fe (III), with citric acid, and an embodiment thereof refers to a complex represented by the following molecular formula: $Fe.(C_6H_8O_7)_x.(H_2O)_y$. In the above molecular formula, x is preferably from 0.75 to 1.10, more preferably from 0.78 to 0.95, more preferably from 0.80 to 0.92, and most preferably from 0.81 to 0.91. According to another embodiment, x is preferably from 0.75 to 1.15, and more preferably from 0.80 to 1.10. In the above molecular formula, y is preferably from 1.8 to 3.2, more preferably from 2.4 to 3.1, and most preferably from 2.7 to 3.1.

The term "about" includes the range of experimental errors, which can normally occur performing a measurement, e.g. ±5% or ±2% or ±1%.

The term "mass" defines the combination of substrates, reagents, solvents, and products on which a physical or chemical transformation is carried out.

The term "excipient" means any substance contained in the final pharmaceutical form other than the active ingredient and which generally may not be therapeutically effective by itself. Excipients are essential for the administration of the active substance, as they allow to deliver the drug to the target site. Excipients are commonly referred to as raw materials entering into the composition of a pharmaceutical preparation with the aim of giving a shape, to facilitate administration and preserve the active ingredient. Furthermore, they contribute to characterize the pharmaceutical preparation from the point of view of appearance, stability, biopharmaceutical profile and acceptability by the patient.

Unless otherwise indicated, in the context of the present invention the percentage and amount of a certain component in a composition are to be referred to the weight of said component with respect to the total weight of the composition. Unless otherwise indicated, in the context of the present invention the indication that a composition "comprises" other one or more components/elements means that the indicated components/elements must be present and also other components may be present, but are not necessarily present, in the composition, in addition to the ones specifically recited. In other words, the indication that a composition "comprises" one or more components does not exclude that the composition consists of, or consists essentially of, the recited component(s).

As used herein, the indication that a compound or composition (e.g.) A is "entirely free" of other substances (or "consists of") means that, within the detection range of the instrument or method being used, no substances other than those specifically indicated can be detected in A.

As used herein, the term "a compound or composition A is essentially free of other substance(s)", or "consists essentially of A", means that only trace amount of substance(s) other than A, if any, can be detected using the analytical methods and techniques known to the person skilled in the art.

Unless otherwise indicated, in the context of the present invention a range of values indicated for a certain parameter, for example the weight of a component in a mixture, includes the upper and the lower limits of the range, e.g. if the content in weight, or in volume, of a component A in a mixture is indicated as "X to Y", the content of A can be X, Y or any of the intermediate values.

By "polymorphically stable" it is meant that the crystalline form of the present invention, when stored (I) at 70° C. under reduced pressure for at least 1 hour (preferably for 5 hours, more preferably for 10 hours, even more preferably for 12 hours), (II) at 60° C. for at least 1 day (preferably for 5 days, more preferably for 10 days, even more preferably for 15 days), (III) at 40° C. and 75% RH for at least 1 day (preferably for 5 days, more preferably for 10 days, even more preferably for 15 days), and/or (IV) at 25-30° C. and 80% RH for at least 1 day (preferably for 5 days, more preferably for 10 days, even more preferably for 15 days), shows no signs of transformation into a different crystalline form as evaluated by the absence of peaks in an X-ray powder diffractogram (XRPD).

By "chemically stable" it is meant that the crystalline form B of the present invention shows no degradation upon storage under stressed conditions, e.g. when stored (I) at 70° C. under reduced pressure for at least 1 hour (preferably for 5 hours, more preferably for 10 hours, even more preferably for 12 hours), (II) at 60° C. for at least 1 day (preferably for 5 days, more preferably for 10 days, even more preferably for 15 days), (III) at 40° C. and 75% RH for at least 1 day (preferably for 5 days, more preferably for 10 days, even more preferably for 15 days), and/or (IV) at 25-30° C. and 80% RH for at least 1 day (preferably for 5 days, more preferably for 10 days, even more preferably for 15 days). "No degradation" means that an analysis of ferric citrate shows no significant worsening of the purity, in terms of formation of new impurities and increase of the content of those already present profile with respect to the initial profile (for example, less than 0.1% area increase).

Unless otherwise indicated, the data relative to the peaks in the XRPD pattern are meant within the common uncertainty due to the instrument measurement, typically +0.2 degrees 2θ, when collected with the Kα radiation of copper ($\lambda$=1.5418 Å). In an embodiment, the present invention relates to a process for the preparation of a high-purity ferric (III) citrate, said process comprising the following steps:

a) bringing into contact ferric acetylacetonate and citric acid in at least one liquid medium so as to obtain a mixture;

b) heating the mixture obtained in step a) to a temperature from 35° C. to the reflux temperature of the at least one medium used so as to obtain a solution of ferric citrate in said medium;

c) bringing into contact the solution of ferric citrate with an antisolvent so as to cause its precipitation; and d) isolating and, optionally, drying it.

Step a) of the process of the present invention the invention comprises the reaction of ferric acetylacetonate (also iron (III) acetylacetonate, often abbreviated Fe(acac)₃) with citric acid, in the presence of a liquid medium, preferably at temperatures from 10° C. to 35° C., more preferably from 15° C. to 30° C., even more preferably from 20° C. to 25° C.

Preferably step a) is carried out by adding at least one liquid medium (preferably comprising water, more preferably consisting of water) to a mass comprising ferric acetylacetonate and citric acid (preferably citric acid monohydrate) so as to obtain a mixture.

Ferric acetylacetonate and citric acid suitable to be used in step a) are commercially available; alternatively, they can be prepared according to standard techniques in organic synthesis.

The molar ratio of ferric acetylacetonate to citric acid is conveniently from 1:0.5 to 1:20. Preferably the molar ratio of ferric acetylacetonate to citric acid is between and optionally includes any two of the following values: 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:3, 1:4, 1:5, 1:6, 1:8, 1:10 or 1:15.

The volume of the at least one liquid medium is normally from 1 mL to 50 mL per gram of ferric acetylacetonate. Preferably the volume of the solvent is between and optionally includes any two of the following values: 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 25 mL, 30 mL, 35 mL, 40 mL or 45 mL per gram of ferric acetylacetonate. More preferably said volume is from 5 mL to 15 mL per gram of ferric acetylacetonate.

Step b) of the method of the present invention includes heating the mixture obtained in step a) to a temperature ranging from 35° C. to the reflux temperature of the at least one liquid medium used so as to obtain a solution of ferric citrate in said medium.

Preferably step b) is carried out at a temperature from 40° C. to 120° C., more preferably from 45° C. to 90° C., even more preferably from 50° C. to 80° C. According to an even more preferred embodiment of this aspect of the invention, said temperature is between and optionally includes any two of the following values: 51° C., 52° C., 53° C., 54° C., 55° C., 56° C., 57° C., 58° C., 59° C., 60° C., 61° C. 62° C., 63° C., 64° C., 65° C., 66° C., 67° C., 68° C., 69° C., 70° C., 71° C., 72° C., 73° C., 74° C., 75° C., 76° C., 77° C., 78° C., or 79° C.

While not intending to be bound by any theory, it is speculated that, in the reaction mixture, ferric acetylacetonate is in equilibrium with ferric (III) citrate, and that the equilibrium can be shifted towards the latter by removing the formed acetylacetone from the reaction mixture. Those of ordinary skill in the art are familiar with suitable removal techniques, e.g., distillation, preferably steam distillation, optionally under reduced pressure.

Thus, according to an embodiment of the present invention, in step b), the formed acetylacetone is removed from the reaction mixture. Particularly, the formed acetylacetone is removed by distillation, more particularly by steam distillation or vacuum distillation.

The removal of acetylacetone has the advantageous effect of ensuring high conversion yields (i.e. at least 80%, preferably at least 85%, more preferably at least 90%, even more preferably at least 95%, said percentages being expressed on a molar basis) of ferric acetylacetonate into ferric citrate.

The removal of acetylacetone under vacuum distillation has the further advantageous effect of preventing the thermal degradation of ferric citrate thus avoiding its subtraction from the reaction mixture and the formation of coordination complex of ferric ions with any by-products resulting therefrom (e.g. aconitic acid, citraconic acid, mesaconic acid, itaconic acid, (meth)acrylic acid and so forth).

A variant of the process object of this aspect of the invention includes an additional and optional step b'), carried out after step b), in which the solution obtained in step b) is cooled or allowed to cool down to a temperature from 20 and 35° C. before bringing it into contact with the antisolvent (according to step c)).

A further variant of the process object of this aspect of the invention includes an additional and optional step b"), carried out after step b) or b'), said step b") comprising removing any undissolved particles from the solution obtained in step b) or b') (preferably by filtration, optionally under reduced pressure).

The following step c) includes mixing the solution of ferric citrate prepared in step b), optionally after having performed step b') and/or b"), with an antisolvent (preferably a water-miscible organic solvent, more preferably a ketone or an alcohol, even more preferably an antisolvend selected from the group consisting of acetone, methanol, ethanol, n-propanol, iso-propanol, and mixtures thereof) in order to precipitate at least a portion of ferric (III) citrate. The antisolvent functions to change the equilibrium solubility of ferric citrate in the solution prepared in step b), b)', or b") such that its concentration is supersaturated (i.e. above its solubility limit). Because ferric citrate is above its equilibrium solubility limit, it precipitates from the solution. Useful antisolvents are those in which ferric citrate is sparingly soluble, such as those in which this compound is soluble in amounts of not more than about 0.1% by weight at 20-25° C.

The volume of the antisolvent is normally from 5 mL to 100 mL per gram of ferric acetylacetonate. Preferably the volume of the solvent is between and optionally includes any two of the following values: 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 21 mL, 22 mL, 23 mL, 24 mL, 25 mL, 26 mL, 27 mL, 28 mL, 29 mL, 30 mL, 31 mL, 32 mL, 33 mL, 34 mL, 35 mL, 36 mL, 37 mL, 38 mL, 39 mL, 40 mL, 41 mL, 42 mL, 43 mL, 44 mL, 45 mL, 46 mL, 47 mL, 48 mL, 49 mL, 50 mL, 55 mL, 60 mL, 65 mL, 70 mL, 75 mL, 80 mL, 85 mL, 90 mL or 95 mL per gram of ferric acetylacetonate.

The volume ratio between the antisolvent and the at least one liquid medium used in step a) is typically from 1:1 to 1:25, preferably from 1:2 to 1:20, more preferably from 1:3 to 1:15, even more preferably from 1:4 to 1:10.

According to a preferred embodiment of this aspect of the invention, the solution of ferric citrate prepared in step b), b') or b") is added to the antisolvent (preferably maintained at a temperature from 0° C. to 35° C., more preferably from 10° C. to 30° C., even more preferably from 20° C. to 25° C.). The direct addition of the antisolvent to the solution of ferric citrate prepared in step b), b') or b"), or the inverse addition of said solution to the antisolvent can be preferably carried out in a single step (i.e. a single addition of the entire volume of the solvent or solution to be added) or, alternatively, in multiple additions. More preferably the solution of ferric citrate prepared in step b), b') or b") is added to the antisolvent dropwise. In a further variant of the process object of this aspect of the invention, an additional and optional step c') is carried out after step c), in which the suspension obtained in step c) is cooled or allowed to cool down to a temperature from 20° C. and 35° C. so as to increase the precipitation rate of ferric (III) citrate.

After precipitation, ferric citrate is recoverd in step d) using known techniques such as filtration or centrifugation and optionally dried, e.g. according to the any of the procedures known in the field, preferably by treating the recovered solid at a temperature from 15° C. to 40° C. (preferably from 20° C. to 30° C.), more preferably under reduced pressure.

According to a second aspect thereof, the present invention provides for a high-purity iron(III) citrate complex obtainable by a process comprising the steps a) to d) reported above. According to a preferred embodiment, the present invention provides for a high-purity iron(III) citrate complex, said complex being substantially free of any organic impurities resulting from the thermal degradation of citric acid (for example aconitic acid, citraconic acid, mesaconic acid, itaconic acid, (meth)acrylic acid).

By "substantially free of any organic impurities resulting from the thermal degradation of citric acid" it is meant that the high-purity iron(III) citrate of the present invention shows a reduced content of those organic impurities resulting, e.g., from the heating of the mixture obtained in step a) (according to step b)). Reduced content of said organic impurities means that a HPLC analysis of the high-purity iron(III) citrate (method 2 detailed below) shows a content of each of these organic impurities preferably lower than 0.20% by weight, more preferably of at maximum 0.15% by weight, even more preferably of at maximum 0.1% by weight, and most preferably of at maximum 0.05% by weight, relative to the total weight.

According to a preferred embodiment of the present invention, the high-purity iron (III) citrate of the invention is amorphous. The term "amorphous form" used herein refers to a halo pattern having diffusive maxima observed via powder X-ray diffraction.

Preferably the high-purity iron (III) citrate is an amorphous powder characterized by an XRPD profile, that when collected with a Kα radiation of copper ($\lambda$=1.5408 Å), comprises at least one of the following features (i) to (iv):
  (i) a halo between 5 and 16° 2θ;
  (ii) a halo between 5 and 16° 2θ and a further halo between 17 and 32° 2θ;
  (iii) a halo between 5 and 16° 2θ, a halo between 17 and 32° 2θ and a further halo between 33 and 50° 2θ; and/or
  (iv) an X-ray powder diffraction pattern as substantially depicted in FIG. 1.

According to a preferred embodiment of the present invention, the high-purity iron (III) citrate has a specific surface area of at maximum 16 $m^2$/g, preferably lower than 15 $m^2$/g, more preferably lower than 14 $m^2$/g, even more preferably lower than 12 $m^2$/g, said specific surface being determined by, for example, BET surface area measurement via nitrogen gas adsorption (relative pressure: 0.05 to 0.3).

A pharmaceutical composition comprising, as an active ingredient, the high-purity iron (III) citrate of the present invention, may be administered to a subject in the form of the pharmaceutical composition alone. Alternatively, the high-purity iron(III) citrate of the present invention can be provided in the form of a medicament (e.g., a pharmaceutical formulation) comprising such compound in combination with at least one member selected from the list comprising (preferably consisting of) a pharmaceutically acceptable carrier, an excipient, a disintegrator, a binder, a fluidizing agent, a diluent, a filler, a buffer, an adjuvant, a stabilizer, a preservative, a lubricant, a solvent, a solubilizer, a suspending agent, an isotonizing agent, a soothing agent and other materials known in the art, and, according to need, other drugs.

In an embodiment, the present invention provides the high purity ferric citrate complex as described above for use in the preparation of a medicament.

In a preferred embodiment, the present invention also provides a method for producing a medicament comprising mixing the high-purity iron (III) citrate as described above with at least one member selected from a pharmaceutically acceptable carrier, an excipient, a disintegrator, a binder, a fluidizing agent, a diluent, a filler, a buffer, an adjuvant, a stabilizer, a preservative, a lubricant, a solvent, a solubilizer, a suspending agent, an isotonizing agent, a soothing agent and other materials known in the art, and, according to need, other drugs.

The term "pharmaceutically acceptable substance" used herein refers to a compound, material, composition, and/or dosage form, which yields an adequate benefit/risk ratio within the scope of appropriate medical decision, which does not cause excessive toxicity, stimulation, allergic reactions, or complications, and which is suitable for use while in contact with tissue of a subject (e.g., a human). Since a carrier, an excipient, and the like can be present together with other ingredients of a pharmaceutical formulation, such substance should be "acceptable".

A pharmaceutical formulation can be adequately provided in unit dosage form and it can be prepared by any method well-known in the field of pharmaceutical technology. Such method comprises a step of mixing the high-purity iron (III) citrate of the present invention with at least one auxiliary ingredient (e.g., a carrier). In general, a pharmaceutical formulation is prepared by homogeneously and coherently mixing an active compound with a finely ground solid carrier and/or a liquid carrier and then generating a product, according to need.

Examples of forms of pharmaceutical formulations (dosage forms) include, but are not limited to, oral formulations, such as tablets, capsules, granules, powders, troches, syrup agents, emulsions, and suspending agents.

Tablets can be produced by optionally adding to the high-purity iron(III) citrate of the present invention at least one auxiliary ingredient described above by a conventional means, such as compression or molding. Compressed tablets can be produced by mixing the high-purity iron(III) citrate of the present invention with at least one member selected from among a binder (e.g., povidone, gelatin, acacia gum, sorbitol, tragacanth, or hydroxypropyl methylcellulose), a filler or diluent (e.g., microcrystalline cellulose or lactose), a lubricant (e.g., calcium stearate, talc, or silica), a disintegrator (e.g., crospovidone, sodium carboxymethyl starch, or crosslinked carboxymethylcellulose sodium), a surfactant, a powder, or a wetting agent (e.g., sodium lauryl sulfate), and a preservative (e.g., methyl p-hydroxybenzoate, propyl p-hydroxybenzoate, or sorbic acid), according to need, and compressing the resultant with a suitable machine. Tablets may be optionally coated or incised. Alternatively, tablets may be prepared so as to achieve sustained release or controlled release of the high-purity iron(III) citrate contained therein. Enteric coating may be optionally applied to tablets, so that the high-purity iron (III) citrate can be released at a region of the gastrointestinal tract other than the stomach.

The invention will be further illustrated by the following examples.

The instruments and methods used to characterize the high-purity iron(III) citrate of the present invention are as follows:

XRPD: Analyses were performed at 20-30° C. by means of a theta/theta vertical scan Bruker AXS D8 Advance high-performance diffractometer. The instrument was equipped with a Cu-Kα X-ray tube operating at 40 kV/40 mA and generating radiation having λ=1.5406 Å. The detector was a linear Lynxeye XE-T position sensitive set at 250 mm from the sample. Powder samples were deposited in the 20 mm×0.5 mm hollow of the sample holder, consisting of a quartz monocrystal zero background plate. A mild grinding of the sample in an agate mortar may be needed to obtain a suitable fine powder. Diffraction data were collected applying the following conditions: angular range 2-80° 2-theta, 0.02°/step scan and 1 second acquisition time. The instrument calibration was verified by means of a NIST SRM 1976b. Data acquisition was performed by means of Bruker Diffraction Measurement Center software. Data elaboration was performed by means of Crystal Impact Match!.

HPLC-UV Method 1:
Column: ZIC®-pHILIC polymeric PEEK 150×4.6 mm, 5 μm (Merck);
Mobile Phase A: ammonium acetate 10 mM in water. pH adjusted to 5.5 with $CH_3CO_2H$;
Mobile Phase B: ammonium acetate 10 mM in methanol. pH adjusted to 6.8 with
$CH_3CO_2H$;
Diluent: water;
Flow Rate: 0.5 mL/min;
Runtime: 60 min;
Column Temperature: 30° C.;
Autosampler Temperature: Ambient;
Injection Volume: 10 μL;
Detection: 235 nm;
Sample concentration: 1 mg/mL;
Elution Program: Gradient

| Time (min.) | A (%) | B (%) |
|---|---|---|
| 0 | 20 | 80 |
| 10 | 20 | 80 |
| 30 | 80 | 20 |
| 40 | 80 | 20 |
| 50 | 20 | 80 |
| 60 | 20 | 80 |

HPLC-UV Method 2:
Column: lnertsil ODS-2 150×4.6 mm, 5 μm (Merck);
Mobile Phase A: 6.8 g of Potassium dihydrogen phosphate in 1 L of water. pH=2.2 ($H_3PO_4$);
Mobile Phase B: methanol;
Diluent: water;
Flow Rate: 1 mL/min;
Runtime: 30 min;
Column Temperature: 25° C.;
Autosampler Temperature: Ambient;
Injection Volume: 50 μL;
Detection: 210 nm;
Sample concentration: 1 mg/mL;
Elution: Isocratic with Mobile Phase A and Mobile Phase B mixture 95:5 (V/V).

EXAMPLES

Example 1

To a mixture comprising 2.0 grams of ferric acetylacetonate and 1.8 grams of citric acid monohydrate, 20 mL water were added at 20-25° C. in a glass flask equipped with thermometer, magnetic stirrer and condenser. The resulting suspension was heated under stirring to 65° C., and maintained at the same temperature until a solution is obtained (about 1 hour). The solution was concentrated under reduced pressure so as to reduce total volume of about one third, then water (15 mL) was added and the solution concentrated again under reduced pressure until complete removal of acetylacetone (as determined by HPLC method 1). The solution was dripped into 26 mL of acetone maintained at 20-25° C. The resulting mixture was maintained under stirring at the same temperature for 3 hours then it was filtered. The solid was washed with acetone, and dried under vacuum at 30° C. thus affording 1.32 grams of ferric citrate as a solid. An aliquot of the solid was analysed by XRPD, obtaining the diffractogram shown in FIG. 1.

Example 2

To a mixture comprising 2.0 grams of ferric acetylacetonate and 1.8 grams of citric acid monohydrate, 20 mL water were added at 20-25° C. in a glass flask equipped with thermometer, magnetic stirrer and condenser. The resulting suspension was heated under stirring to 65° C., and maintained at the same temperature until a solution is obtained (about 1 hour). The solution was concentrated under reduced pressure so as to reduce total volume of about one third, then water (15 mL) was added and the solution concentrated again under reduced pressure until complete removal of acetylacetone (as determined by HPLC method 1). 26 mL of acetone were added thereto and the mixture was maintained under stirring at 20-25° C. for 3 hours. After filtration, the solid was washed with acetone and dried under vacuum, thus affording 1.28 grams of ferric citrate as a solid.

An aliquot of the solid was analysed by XRPD, obtaining a diffractogram corresponding to that shown in FIG. 1.

The following pages of the description refer to some of the embodiments of the invention listed as separate items:

1. Process for the preparation of a high-purity ferric (III) citrate, said process comprising the following steps:
    a) bringing into contact ferric acetylacetonate and citric acid in at least one liquid medium so as to obtain a mixture;
    b) heating the mixture obtained in step a) to a temperature from 35° C. to the reflux temperature of the at least one medium used so as to obtain a solution of ferric citrate in said medium;
    c) bringing into contact the solution of ferric citrate with an antisolvent so as to cause its precipitation; and
    d) isolating and, optionally, drying it.
2. The process of item 1, in which the at least one liquid medium used in step a) comprises water.
3. The process of any one of items 1 or 2, in which the at least one liquid medium used in step a) consists of water.
4. The process of any one of items 1 to 3, in which step a) is carried out at a temperature from 10° C. to 35° C.
5. The process of any one of items 1 to 4, in which, in step a), the at least one liquid medium is added to a mixture comprising citric acid and ferric acetylacetonate.
6. The process of any one of items 1 to 5, in which citric acid monohydrate is used in step a).
7. The process of any one of items 1 to 6, in which, in step a), the molar ratio of ferric acetylacetonate to citric acid is from 1:0.5 to 1:20.
8. The process of any one of items 1 to 7, in which, in step a), 1 to 50 mL of liquid medium are used per gram of ferric acetylacetonate.

9. The process of any one of items 1 to 8, in which, in step b), the formed acetylacetone is removed from the reaction mixture.
10. The process of item 9, in which, the formed acetylacetone is removed by distillation.
11. The process of any one of items 9 or 10, in which, the formed acetylacetone is removed by steam distillation or vacuum distillation.
12. The process of any one of items 1 to 11, in which step b) is carried out at a temperature from 40° C. to 120° C.
13. The process of any one of items 1 to 12, in which step b) is carried out at a temperature from 45° C. to 90° C.
14. The process of any one of items 1 to 13, in which step b) is carried out at a temperature from 50° C. to 80° C.
15. The process of any one of items 1 to 14, in which an additional step b') is carried out after step b), said step b') comprising cooling or allowing to cool the solution obtained in step b) to a temperature from 20 to 35° C.
16. The process of item 15, in which an additional step b") is carried out after step b'), said step b") comprising removing any undissolved particles from the solution obtained in step b').
17. The process of any one of items 1 to 14, in which an additional step b") is carried out after step b), said step b") comprising removing any undissolved particles from the solution obtained in step b).
18. The process of any one of items 1 to 17, in which the antisolvent used in step c) is a water-miscible organic solvent.
19. The process of any one of items 1 to 18, in which the antisolvent used in step c) is selected from the list consisting of ketones and alcohols.
20. The process of any one of items 1 to 19, in which the antisolvent used in step c) is selected from the list consisting of acetone, methanol, ethanol, n-propanol, iso-propanol, and mixtures thereof.
21. The process of any one of items 1 to 20, in which, in step c), 5 to 100 mL of antisolvent are used per gram of ferric acetylacetonate.
22. The process of any one of items 1 to 21, in which, in step c), the volume ratio between the antisolvent and the at least one liquid medium is from 1:1 to 1:25.
23. The process of any one of items 1 to 22, in which, in step c), the solution of ferric citrate is added to the antisolvent.
24. The process of any one of items 1 to 23, in which, in step c), the solution of ferric citrate is added to the antisolvent maintained at a temperature from 0° C. to 35° C.
25. The process of any one of items 23 or 24, in which the solution of ferric citrate is added dropwise to the antisolvent.
26. The process of any one of items 1 to 25, in which an additional step c') is carried out after step c), said step c') comprising cooling or allowing to cool the suspension obtained in step c) to a temperature form 20° C. to 35° C.
27. The process of any one of items 1 to 26, in which, in step d), ferric citrate is isolated by filtration.
28. The process of any one of items 1 to 27, in which, in step d), ferric citrate is dried at a temperature from 15° C. to 40° C.
29. The process of any one of items 1 to 28, in which, in step d), ferric citrate is dried under reduced pressure.
30. High purity ferric citrate complex obtainable by the process of any one of items 1 to 29.
31. High purity ferric citrate complex, said complex being substantially free of any organic impurities resulting from the thermal degradation of citric acid.
32. High purity ferric citrate complex of any one of items 30 or 31, said complex having a specific surface area of at maximum 16 m$^2$/g.
33. High purity ferric citrate complex of any one of items 30 to 32, said complex being amorphous.
34. High purity ferric citrate complex of any one of items 30 to 33, said complex being characterized an XRPD profile, that when collected with a Kα radiation of copper (λ=1.5408 Å), comprises at least one of the following features (i) to (iv):
    (i) a halo between 5 and 16° 2θ;
    (ii) a halo between 5 and 16° 2θ and a further halo between 17 and 32° 2θ;
    (iii) a halo between 5 and 16° 2θ, a halo between 17 and 32° 2θ and a further halo between 33 and 50° 2θ; and
    (iv) an X-ray powder diffraction pattern as substantially depicted in FIG. 1.
35. High purity ferric citrate complex of any one of items 30 to 34 for use as a medicament.
36. Pharmaceutical composition comprising the high purity ferric citrate complex of any one of items 30 to 34.
37. Pharmaceutical composition comprising the high purity ferric citrate complex of any one of items 30 to 34 and at least one pharmaceutically acceptable carrier.
38. Pharmaceutical composition of any one of items 36 or 37 for use in medicine.

The invention claimed is:
1. A process for the preparation of a high-purity ferric (III) citrate, said process comprising the following steps:
    a) bringing into contact ferric acetylacetonate and citric acid in at least one liquid medium so as to obtain a mixture;
    b) heating the mixture obtained in step a) to a temperature from 35° C. to the reflux temperature of the at least one medium used so as to obtain a solution of ferric citrate in said medium;
    c) bringing into contact the solution of ferric citrate with an antisolvent so as to cause its precipitation; and
    d) isolating and, optionally, drying it.
2. The process of claim 1, in which the at least one liquid medium used in step a) comprises, or consists of, water.
3. The process of claim 1, in which, in step b), the formed acetylacetone is removed from the reaction mixture.
4. The process of any claim 1, in which step b) is carried out at a temperature from 40° C. to 120° C.
5. The process of claim 1, in which an additional step b') is carried out after step b), said step b') comprising cooling or allowing to cool the solution obtained in step b) to a temperature from 20 to 35° C.
6. The process of claim 1, in which the antisolvent used in step c) is a water-miscible organic solvent.
7. The process of claim 1, in which, in step c), the solution of ferric citrate is added to the antisolvent.
8. The process of claim 2, in which, in step b), the formed acetylacetone is removed from the reaction mixture.
9. The process of claim 2, in which step b) is carried out at a temperature from 40° C. to 120° C.
10. The process of claim 2, in which an additional step b') is carried out after step b), said step b') comprising cooling or allowing to cool the solution obtained in step b) to a temperature from 20 to 35° C.
11. The process of claim 2, in which the antisolvent used in step c) is a water-miscible organic solvent.

12. The process of claim 2, in which, in step c), the solution of ferric citrate is added to the antisolvent.

\* \* \* \* \*